United States Patent [19]

Kuraoka et al.

[11] Patent Number: 4,539,824
[45] Date of Patent: Sep. 10, 1985

[54] APPARATUS FOR CONTINUOUSLY FREEZING LIVER PIECE

[75] Inventors: Yasuo Kuraoka; Nobuo Sakao, both of Yatabe, Japan

[73] Assignee: Hoxan Corporation, Sapporo, Japan

[21] Appl. No.: 658,628

[22] Filed: Oct. 9, 1984

[30] Foreign Application Priority Data

Mar. 15, 1984 [JP] Japan .............................. 59-37096[U]

[51] Int. Cl.$^3$ .............................................. F25D 25/04
[52] U.S. Cl. ........................................ 62/380; 62/63; 62/303; 62/374; 165/94; 198/635; 426/524
[58] Field of Search ................... 62/63, 266, 374, 375, 62/380, 303, 354; 198/635; 165/94; 426/524

[56] References Cited

U.S. PATENT DOCUMENTS

| | | | |
|---|---|---|---|
| 2,758,445 | 8/1956 | Saxe | 62/380 |
| 2,974,497 | 3/1961 | Carpenter et al. | 62/63 |
| 3,302,423 | 2/1967 | Morrison | 62/374 |
| 3,395,549 | 8/1968 | Grimes | 62/63 |
| 3,809,209 | 5/1974 | Akesson | 198/635 |
| 4,378,873 | 4/1983 | Cloudy | 62/380 |

Primary Examiner—Ronald C. Capossela
Attorney, Agent, or Firm—George B. Oujevolk

[57] ABSTRACT

An apparatus for continuously freezing liver pieces which comprises a freezing box having an inlet and an outlet, a conveyor movable from the inlet to the outlet of the freezing box and having a mesh belt, a number of nozzles provided laterally through the box at the upside of the mesh belt of the conveyor for blowing gaseous helium, a supplying guide portion formed at the head of the inlet at the upside of the mesh belt for supplying and placing the liver pieces, a rotatable roller journaled at the striking-off and exhausting portion disposed inside the striking-off and exhausting portion at the head of the outlet at the upside of the mesh belt in an outside contacting state laterally of the mesh belt, the roller having a number of striking-off projections projected from the surface thereof for striking-off the frozen liver pieces on the mesh belt by the insertion of the projections into the mesh belt. Thus, the apparatus can efficiently freeze the liver piece instantaneously without irregularity by instantaneously blowing helium gas in contact with the liver piece to obtain a frozen liver capable of performing the function of the liver at the thawed time.

3 Claims, 2 Drawing Figures

APPARATUS FOR CONTINUOUSLY FREEZING LIVER PIECE

BACKGROUND OF THE INVENTION

This invention relates to an artificial liver adapted for an artificial liver supplementing apparatus used for subsidizing the function of the liver of a patient who has a liver disease such as a severe hepatitis and, more particularly, to an apparatus for freezing a liver piece to freeze a living liver so as to endure a preservation of the artificial liver for a long period of time and to be able to be used timely as required.

The applicant has invented the following invention and filed a patent application as a freezing method capable of enduring a preservation of a liver for a long period of time and allowing the liver to sufficiently perform the function of the liver at the time of thawing and using the liver.

The filed invention is a method of freezing a liver by cutting a liver removed from a human being or an animal, from which blood is removed into fine cubic pieces and freezing the liver pieces with helium gas.

It is confirmed that the frozen artificial liver obtained by the method of this prior invention could perform the excellent action of supplementing the function of the liver. This is because the liver was finely cut, different from the conventional liver which was sliced into thin large-sized piece, substantially all fine liver pieces out from the surface to the central interior of the liver can perform the function of the liver and helium gas is employed instead of liquid helium without using liquefied nitrogen gas.

More particularly, this is considered because the boiling point of the liquid helium is cryogenic, approx. $-269°$ C., the specific heat of the helium gas is 5.23 (J/g.C.°), which is approx. five times as compared with the nitrogen gas, with the result that the freezing velocity is very high such as $1000°$ C./mm, and the tissue of the liver can be frozen without being destroyest by utilizing such high freezing velocity.

SUMMARY OF THE INVENTION

An object of the present invention is to provide an apparatus for continuously freezing a liver piece to execute the above-described freezing method, which can efficiently freeze the liver piece instantaneously without irregularity by instantaneously blowing helium gas in contact with the liver piece to obtain a frozen liver capable of performing the function of the liver at the thawed time and to also continuously and efficiently freeze the liver.

The above and other related objects and features of the invention will be apparent from a reading of the following description of the disclosure found in the accompanying drawings and the novelty thereof pointed out in the appended claims.

DESCRIPTION OF THE PREFERRED EMBODIMENTS

An apparatus for continuously freezing a liver piece according to the present invention will now be described with respect to the embodiment disclosed in the accompanying drawings.

Figure 1:
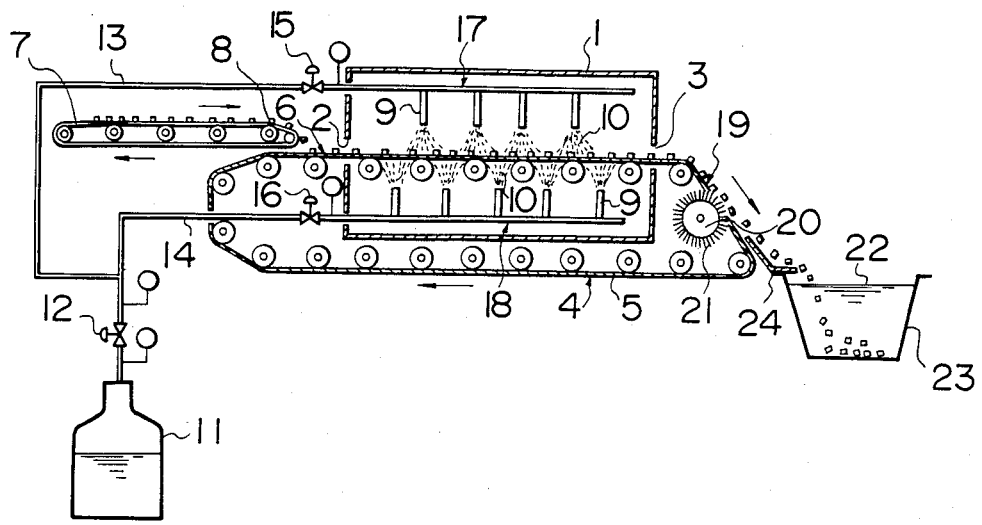
FIG. 1 is an explanatory longitudinal sectional side view of an embodiment of an apparatus for continuously freezing a liver piece constructed according to the present invention.

As shown in FIG. 1, a freezing box 1, which is preferably thermally insulated, is opened at an inlet 2 and an outlet 3 at both left and right sides, and the upper side of a mesh belt 5 of a conveyor 4 which is movable from the inlet 2 to the outlet 3 is laterally provided through the box 1.

A supplying guide portion 6 is horizontally formed before the inlet 2 at the upside of the mesh belt 5. Liver pieces 8 supplied onto a belt conveyor 7 adjacent to the supplying guide portion 6 are supplied onto the guide portion 6. The liver pieces 8 thus placed on the mesh belt 5 are introduced into the freezing box 1 by the operation of the conveyor 4.

Further, a number of nozzles 9 are provided in the box 1 to blow gaseous helium 10 therefrom. In the embodiment exemplified in the drawings, upside and downside conduits 13 and 14 are branched from a helium container 11 through a pressure regulator 12, and through flow rate control valves 15 and 16 to the nozzles 9 of upside and downside nozzle groups 17 and 18. The nozzles 9 of the nozzle groups 17 and 18 are respectively arranged to blow gaseous helium toward the upper and inner surface sides of the mesh belt 5.

Figure 2:
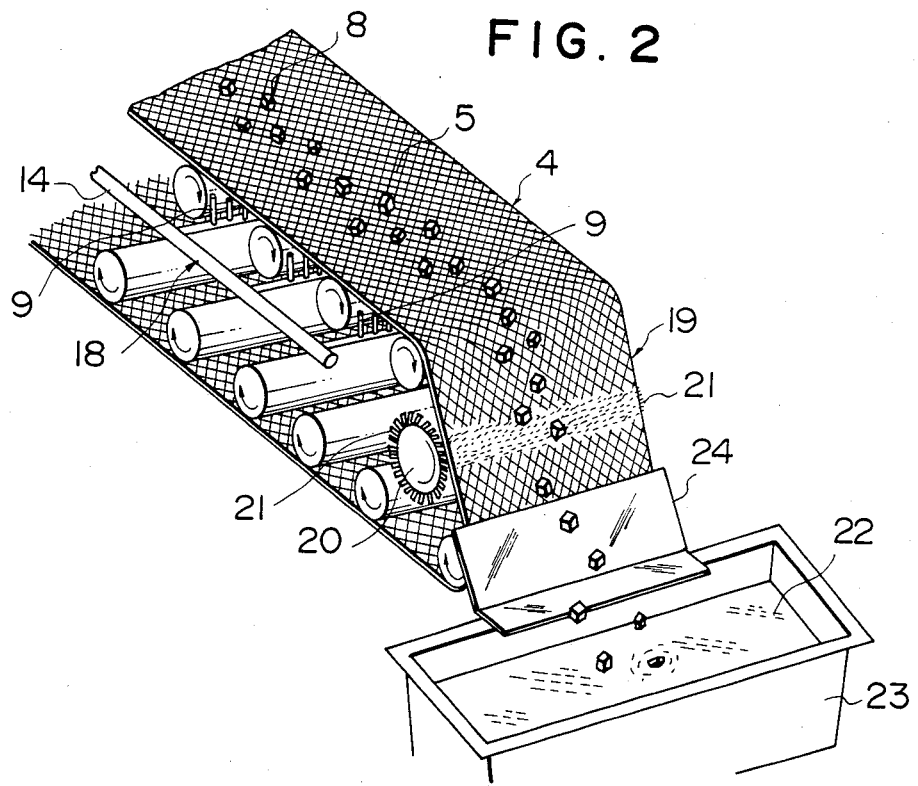
FIG. 2 is an enlarged perspective view of the essential part of the apparatus, illustrating the end side of an endless belt conveyor.

Further, an striking-off and exhausting portion 19 is formed at the head of the outlet 3 in the conveyor 4. In the embodiment exemplified in the drawings, the mesh belt 5 in the conveyor is arranged obliquely in such a manner that the head side is downwardly inclined. As apparent in FIG. 2, a rotatable roller 20 which is journaled in an outside contacting state is provided laterally of the mesh belt 5 inside the belt 5, and a number of striking-off projections 21 are radially projected like a brush from the roller 20. The projections 21 are inserted into the mesh belt 5 at the contacting positions with the mesh belt 5 to be extended and passed into the upper surface side of the belt 5.

When the mesh belt 5 is rotated in a direction of an arrow in FIG. 1 by operating the conveyor 4, the roller 20 is rotated in synchronization with the mesh belt 5 through the engagement of the exfoliating projections 21 of the roller 20 with the mesh belt 5. In this case, it is noted that the roller 20 may be rotatably driven by a power source.

A storage tank 23 for liquefied nitrogen 22 is provided in an open state at the lower head side of the striking-off and exhausting portion 19. Reference numeral 24 designates an L-shaped bent guide retainer.

In operation of the apparatus thus constructed as described above, the liver pieces 8 are supplied onto the moving belt conveyor 7, transferred to the supplying guide portion 6 at the upside of the mesh belt 5 of the conveyor 4 for moving the liver pieces 8, introduced into the freezing box 1, and instantaneously frozen by injecting the gaseous helium 10 from the nozzles 9.

The frozen liver pieces 8 are fed out of the outlet 3 of the freezing box 1 to the exfoliating and striking-off portion 19. In this case, the liver pieces 8 are adhered to the mesh belt 5 due to freezing, and located at the striking-off and exhausting portion 19 disposed at the downwardly inclined position. Thus, the liver pieces 8 are protruded from the inside of the mesh belt 5 by the striking-off projections 21 of the roller 20 protruded from the mesh belt 5 through the mesh belt 5, thus taken-off from the mesh belt 5, then dropped from the mesh belt 5 along the guide retainer 24, and cast and received into the liquid nitrogen 22 in the storage tank 23. The liver pieces 8 are preserved in place in this state.

According to the present invention as described above, the present invention provides the apparatus for continuously freezing the liver pieces, which comprise a freezing box 1 having an inlet 2 and an outlet 3, a conveyor 4 movable from the inlet 2 to the outlet 3 of the freezing box 1 and having a mesh belt 5, a number of nozzles 9 provided laterally through the box 1 at the upside of the mesh belt 5 of the conveyor 4 for blowing gaseous helium 10, a supplying guide portion 6 formed at the head of the inlet 2 at the upside of the mesh belt 5 for supplying and placing the liver pieces 8, a rotatable roller 20 journaled at the striking-off and exhausting portion 19 disposed inside the striking-off and exhausting portion 19 at the head of the outlet at the upside of the mesh belt 5 in an outside contacting state laterally of the mesh belt 5, the roller 20 having a number of striking-off projections 21 projected from the surface thereof for striking-off the frozen liver pieces on the mesh belt 5 by the insertion of the projections 21 into the mesh belt 5. Therefore, the liver pieces 8 placed on the mesh belt 5 are sufficiently contacted with the gaseous helium, and accordingly instantaneously frozen completely, and the liver pieces thus frozen onto the mesh belt 5 can be conveniently taken-off by the striking-off projections 21 on the roller 20. Consequently, the apparatus of the invention does not take a plenty of time to move the frozen liver pieces into refrigerant for preserving the liver pieces such as liquefied nitrogen or the like, and can continuously and efficiently freeze the liver pieces as desired.

What is claimed is:

1. An apparatus for continuously freezing liver pieces comprising:
 a freezing box having an inlet and an outlet,
 a conveyor movable from the inlet to the outlet of said freezing box and having a mesh belt,
 a number of nozzles provided laterally through the box at the upside of the mesh belt of said conveyor for injecting gaseous helium,
 a supplying guide portion formed at the head of the inlet at the upside of the mesh belt for supplying and placing the liver pieces,
 a rotatable roller journaled at the striking-off and exhausting portion disposed inside the striking-off and exhausting portion at the head of the outlet at the upside of the mesh belt in an outside contacting state laterally of the mesh belt, said roller having a number of striking-off projections projected from the surface thereof for striking-off the frozen liver pieces on the mesh belt by the insertion of the projections into the mesh belt.

2. The apparatus according to claim 1, wherein said nozzles are arranged to inject gaseous helium toward the upper and inner surface sides of the mesh belt.

3. The apparatus according to claim 1, wherein said striking-off and exhausting portion is downwardly inclined to drop the exfoliated frozen liver pieces toward the head side disposed with a storage tank of liquid nitrogen into the storage tank.

* * * * *